US00PP17757P2

(12) United States Plant Patent
Shiotsuki

(10) Patent No.: US PP17,757 P2
(45) Date of Patent: May 22, 2007

(54) ***PENTAS* PLANT NAMED 'NAKPEN003'**

(50) Latin Name: *Pentas lanceolata*
Varietal Denomination: NAKPEN003

(75) Inventor: Shouji Shiotsuki, Ashigara Kami-gun (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 11/337,765

(22) Filed: Jan. 23, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—Jondle & Associates P.C.

(57) ABSTRACT

A new *Pentas* plant particularly distinguished by pink flowers, a large flower cluster size, upright form, and a compact and branching growth habit is disclosed.

1 Drawing Sheet

Genus and species: *Pentas lanceolata.*
Variety denomination: 'NAKPEN003'.

BACKGROUND OF THE NEW PLANT

The present invention comprises a new and distinct cultivar of *Pentas,* botanically known as *Pentas lanceolata,* and hereinafter referred to by the cultivar name 'NAKPEN003'. The new cultivar originated from a hybridization made in 1995 in Fujisawa, Japan. An initial cross was made between a commercial female *Pentas* plant designated 'New Pink' (unpatented) having pink flowers, large flower clusters, a long flowering period and a glossy foliage, and a commercial male *Pentas* plant designated 'New Rose' (unpatented) having dark pink flowers, large flower clusters, a long flowering period and a branching growth habit. The $F_1$ seeds produced by the hybridization were sown in a greenhouse in 1996 and later transplanted to an outdoor trial. The $F_1$ plants were evaluated and selected based on compact growth habit, branching, and large flower clusters. The $F_2$ generation seed was sown in 1997, the $F_3$ generation seed was sown in 1998, and the $F_4$ generation seed was sown in 1999 and later transplanted to an outdoor trial. A single plant selection was chosen for further evaluation and for asexual propagation in 1999 based on its pink flower color, branching and compact growth habit, and large flower clusters.

This single plant selection was asexually propagated and further evaluated in Fujisawa, Japan in 2001 in an indoor pot trial and an outdoor trial to confirm the uniformity and stability of its characteristics. In 2003, another indoor pot trial and outdoor trial were performed to confirm uniqueness. The plant was also trialed in Salinas, Calif. The selection subsequently was named 'NAKPEN003' and found to retain its distinctive characteristics through successive asexual propagations.

Plant Breeder's Rights for this cultivar were applied for in Canada on Apr. 4, 2005.

SUMMARY OF THE INVENTION

The following are the most outstanding and distinguishing characteristics of this new cultivar when grown under normal horticultural practices in Salinas, Calif.

1. Pink flower color;
2. Large flower cluster size;
3. A branching growth habit; and
4. An upright and compact plant habit.

DESCRIPTION OF PHOTOGRAPHS

This new *Pentas* plant is illustrated by the accompanying photographs which show overall plant habit including blooms, buds, and foliage of the plant; the colors shown are as true as can be reasonably obtained by conventional photographic procedures.

DESCRIPTION OF THE NEW CULTIVAR

Figure 1:
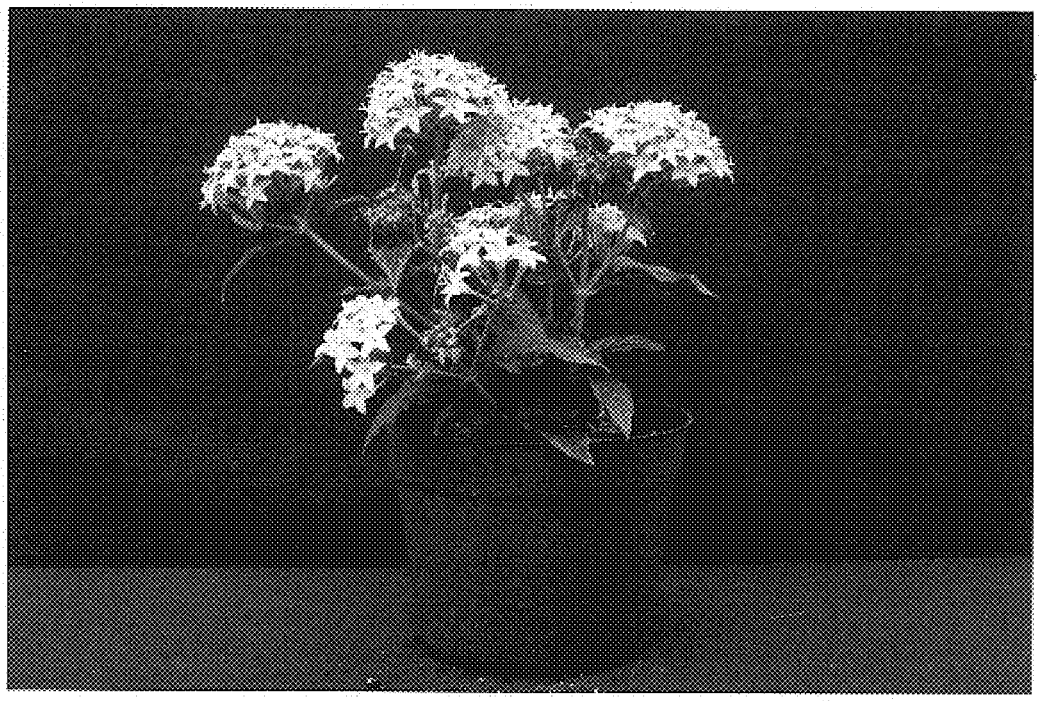
FIG. 1 shows the overall plant habit, including blooms, buds, mature foliage, and plant habit.
Figure 2:
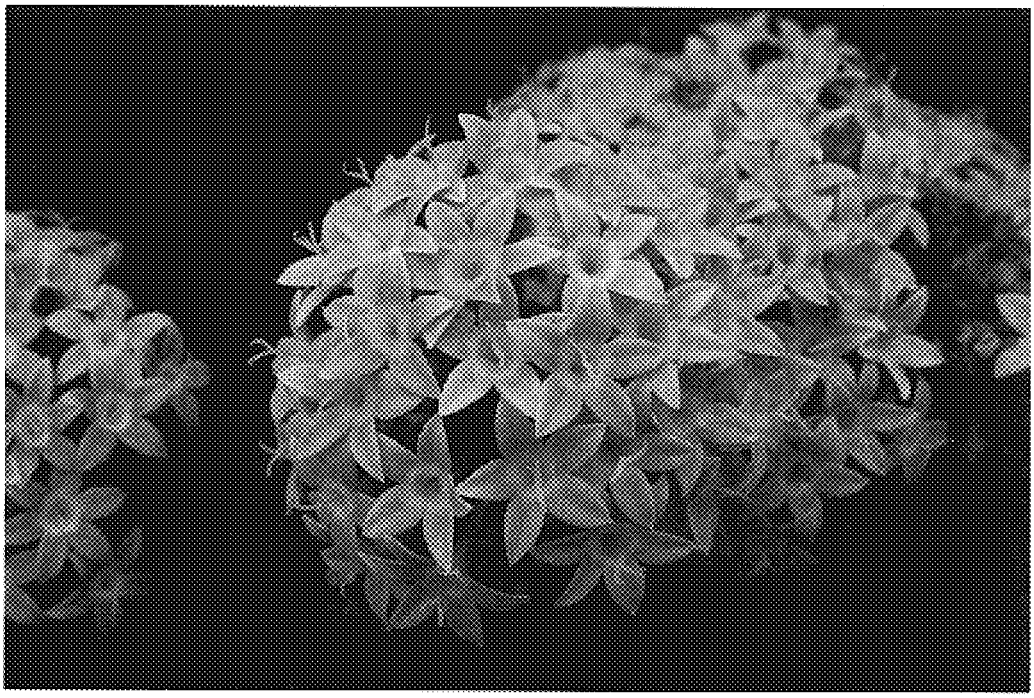
FIG. 2 shows a close-up of mature inflorescences.

The following detailed description sets forth the distinctive characteristics of 'NAKPEN003'. The data which define these characteristics were collected from asexual reproductions carried out in Salinas, Calif. The data were obtained from plants grown about four months from propagation by terminal cuttings under greenhouse conditions. The following traits and characteristics describe the new variety. Color references are to The Royal Horticultural Society Colour Chart, $4^{th}$ edition. Anatomic labels are from *The Cambridge Illustrated Glossary of Botanical Terms,* by M. Hickey and C. King, Cambridge University Press.

DETAILED BOTANICAL DESCRIPTION OF THE NEW PLANT

Classification:
*Family.*—Rubiaceae.
*Botanical name.*—*Pentas lanceolata.*
*Common name.*—*Pentas.*

Parentage:
*Female parent of the initial cross.*—'New Pink' an unpatented pink-flowered *Pentas* plant.
*Male parent of the initial cross.*—'New Rose' an unpatented dark-pink flowered *Pentas* plant.

Growth:

*Time to produce a rooted cutting.*—The terminal 1.0 to 1.5 inches of an actively growing stem was excised. The vegetative cuttings were propagated in five to six weeks. The base of the cuttings were dipped for one to two seconds in a 1:9 solution of DIP 'N GROW (1 part solution: 9 parts water) root inducing solution immediately prior to placing into the cell trays. Cuttings were placed into plastic cell trays having 98 cells, and containing a moistened peat moss-based growing medium. The cuttings were misted with water from overhead for 10 seconds every 30 minutes until sufficient roots were formed.

*Environmental conditions for plant growth.*—Rooted cuttings were transplanted and grown in 20-cm diameter plastic pots in a glass greenhouse located in Salinas, Calif. Pots contained a peat moss-based growing medium. Soluble fertilizer containing 20% nitrogen, 10% phosphorous and 20% potassium was applied once a day or every other day by overhead irrigation. Pots were top-dressed with a dry, slow release fertilizer containing 20% nitrogen, 10% phosphorous and 18% potassium. The typical average air temperature was 24° C.

Plant description:

*Life cycle.*—Annual.

*Habit.*—Upright and compact with several basal branches.

*Height.*—18.0 cm to 20.0 cm.

*Spread (including flowers).*—23.5 cm to 27.5 cm.

*Time to produce a rooted cutting.*—About 5 weeks.

*Time to produce a finished flowering plant.*—8 to 10 weeks.

*Flowering requirements.*—Will flower so long as the day length is greater than 12 hours and the temperature exceeds 13° C.

*Preferred propagation temperature.*—18° C. to 24° C.

Branches:

*Number.*—10 per plant.

*Length.*—15.5 cm to 17.0 cm.

*Diameter.*—0.3 cm to 0.4 cm.

Stems:

*Description.*—Strong; circular cross-section.

*Length.*—1.0 cm from soil line to first node.

*Diameter.*—0.4 cm.

*Internode length.*—2.8 cm to 4.9 cm.

*Color.*—RHS 144A (yellow-green).

*Anthocyanin.*—Absent.

*Texture.*—Heavily pubescent.

*Pubescence color.*—RHS N155A (white).

Leaves:

*Arrangement.*—Opposite.

*Shape.*—Lanceolate.

*Apex.*—Acuminate.

*Base.*—Attenuate.

*Margin.*—Entire to undulate.

*Size.*—Length: 7.1 cm to 7.5 cm. Width: 2.9 cm to 3.5 cm.

*Color.*—Upper surface: Closest to RHS 139A (green). Lower surface: RHS 138B (green).

*Variegation.*—Absent.

*Venation.*—Type: Pinnate. Color: Upper surface: RHS 144C (yellow-green). Lower surface: RHS 144C (yellow-green).

*Fragrance.*—Absent.

*Texture.*—Dull.

*Surface pubescence.*—Heavy.

*Surface pubescence color.*—RHS N155A (white).

*Petiole length.*—0.2 cm to 0.3 cm.

*Petiole color.*—RHS 144C (yellow-green).

Flower bud:

*Texture.*—Slightly pubescent.

*Size.*—Length: 0.5 cm to 0.6 cm. Diameter: 0.1 cm.

*Shape.*—Elliptical, longitudinal cross-section.

*Color.*—RHS 144D (yellow-green).

Flowers:

*Inflorescence type.*—Corymbose; 4 to 5 corymbs in full bloom per plant.

*Number of flowers per corymb.*—60 to 90 flowers and buds.

*Corymb diameter.*—7.0 cm to 8.0 cm.

*Corymb depth.*—4.5 cm to 6.0 cm.

*Fragrance.*—Absent.

*Corolla.*—Shape. Salverform with 5 radial petals. Diameter: 2.0 cm. Depth: 1.5 cm to 1.6 cm. Tube diameter: 0.4 cm to 0.5 cm.

*Calyx (sepals).*—Shape: 5, fused. Apex: Acute. Base: Attenuate. Margin: Entire. Color: RHS 139A (green).

*Penduncle.*—Color: RHS 62B (red-purple). Length: 1.7 cm to 1.8 cm. Diameter: 01. cm.

*Petals.*—Texture: Glabrous. Size: Length: 0.6 cm to 0.7 cm. Width: 0.4 cm to 0.5 cm. Shape: Lanceolate. Apex: Acute. Margin: Entire. Color: Upper surface: RHS 62B (red-purple). Lower surface: RHS 62B (red-purple) at mid-vein fading to RHS N155A (white) at the edges. Corolla throat: RHS N155A (white).

Reproductive organs:

*Stamens.*—Quantity: 5. Filament: Color: RHS 4A (yellow). Length: 0.3 cm. Diameter: Less than 0.1 cm. Anther color: RHS 4A (yellow). Pollen amount: Abundant. Pollen color: RHS 4A (yellow). Pollen description: Powdery.

*Pistils.*—Quantity: 1, split into 2 stigmas. Length: 2.3 cm to 2.5 cm. Stigma color: RHS 136D (green). Style color: RHS N155A (white).

Fruit and seed set: Has not been observed.

Disease and insect resistance: No particular resistance or susceptibility has been observed.

COMPARISON WITH COMMERCIAL CULTIVARS

'NAKPEN003' is a new and unique variety of *Pentas* owing to its compact, branching growth habit, upright form, large flower cluster size, and pink flower color. Table 1 below shows 'NAPKEN003' compared to the lines of the initial cross.

TABLE 1

Comparison with Lines of Initial Cross 'New Rose' and 'New Pink'

| Characteristic | 'NAPKEN003' | Male: 'New Rose' | Female: 'New Pink' |
|---|---|---|---|
| Flower color | Pink | Dark Pink | Pink |
| Plant growth habit | Upright, branching, compact | Branching | Upright |

'NAKPEN003' is similar to the commercial *Pentas* variety 'New Look Rose' (unpatented) however, there are differences as listed in the table below:

TABLE 2

Comparison of Characteristics between 'NAKPEN003' and 'New Look Rose'

| Characteristic | 'NAKPEN003' | 'New Look Rose' |
|---|---|---|
| Plant growth habit | Upright, branching and compact | Mounding |
| Flower color | Pink | Rose |
| Flower cluster size | Large | Medium |

I claim:

1. A new and distinct cultivar of *Pentas* plant as shown and described herein.

* * * * *